(12) United States Patent
Yang et al.

(10) Patent No.: US 6,878,110 B2
(45) Date of Patent: Apr. 12, 2005

(54) SURGICAL INSTRUMENTS AND METHOD FOR CREATING ANATOMIC WORKING SPACE IN MINILAPAROTOMY PROCEDURE

(76) Inventors: Seung Choul Yang, 447-3, Dohwa-dong, Nam-gu, Inchon-shi, 402-060 (KR); Koon Ho Rha, 9-1107, Shindonga Apt., Seobingo-dong, Yongsan-gu, Seoul, 140-751 (KR)

( * ) Notice: Subject to any disclaimer, the term of this patent is extended or adjusted under 35 U.S.C. 154(b) by 89 days.

(21) Appl. No.: 10/043,178

(22) Filed: Jan. 14, 2002

(65) Prior Publication Data

US 2003/0135093 A1 Jul. 17, 2003

(51) Int. Cl.$^7$ .................................................. A61B 1/32
(52) U.S. Cl. ...................................................... 600/204
(58) Field of Search ................................ 600/184, 201, 600/204, 205, 210, 213, 235, 214, 217; 606/167, 181, 184, 185, 223; 30/30

(56) References Cited

U.S. PATENT DOCUMENTS

| | | | | |
|---|---|---|---|---|
| 1,708,578 A | * | 4/1929 | Hyde ........................... | 600/217 |
| 4,026,338 A | * | 5/1977 | Goebel ......................... | 81/441 |
| 4,180,075 A | * | 12/1979 | Marinoff ..................... | 606/166 |
| 5,176,129 A | * | 1/1993 | Smith .......................... | 600/219 |
| 5,299,563 A | * | 4/1994 | Seton ........................... | 600/215 |
| 5,352,219 A | * | 10/1994 | Reddy ............................. | 606/1 |
| 5,411,510 A | * | 5/1995 | Fugo ............................ | 606/166 |
| 5,429,121 A | * | 7/1995 | Gadelius ...................... | 600/217 |
| 5,569,271 A | * | 10/1996 | Hoel ............................ | 606/148 |
| 5,891,017 A | * | 4/1999 | Swindle et al. .............. | 600/205 |
| 5,910,147 A | * | 6/1999 | Rosenberg et al. ........... | 606/131 |
| 5,931,777 A | * | 8/1999 | Sava ............................ | 600/213 |
| 6,309,219 B1 | * | 10/2001 | Robert ......................... | 433/144 |
| 6,454,783 B1 | * | 9/2002 | Piskun ......................... | 606/185 |
| 6,626,670 B1 | * | 9/2003 | Lerner et al. ................ | 433/122 |
| 6,705,865 B1 | * | 3/2004 | Szymaitis .................... | 433/141 |

\* cited by examiner

*Primary Examiner*—Eduardo C. Robert
*Assistant Examiner*—Anu Ramana
(74) *Attorney, Agent, or Firm*—Morgan Lewis & Bockius LLP

(57) ABSTRACT

A method for creating an anatomic working space in a body for a minilaparotomy procedure includes forming a minilaparotomy opening in the body, forming a trocar opening in the body, inserting a trocar into the trocar opening, introducing a telescope through the trocar to observe a first tissue to be surgically treated, inserting at least one first piercing retractor into the body through the opening, wherein the piercing retractor has first and second end portions, puncturing a wall of the body by the first end portion of the first piercing retractor, and lifting the wall of the body and moving around by using the first piercing retractor until a desirable anatomic working space is created in the body. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims.

25 Claims, 9 Drawing Sheets

SURGICAL INSTRUMENTS AND METHOD FOR CREATING ANATOMIC WORKING SPACE IN MINILAPAROTOMY PROCEDURE

BACKGROUND OF THE INVENTION

1. Field of the Invention

The present invention relates to an apparatus and method for use in medical procedures, and more particularly, to surgical instruments and a method for creating an anatomic working space in a minilaparotomy procedure. Although the present invention is suitable for a wide scope of applications, it is particularly suitable for minimizing a laparoscopic incision and allowing a laparotomy procedure without gas insufflation.

2. Discussion of the Related Art

Creating an anatomic working space within a body is important in both open surgical procedures and laparoscopic procedures. In the open surgical procedures, a patient's skin and body wall are incised in order to view the surgical area. In addition, retracting devices should be used to lift up the body wall for securing an anatomic working space during the operative procedure.

On the other hand, the patient's abdominal wall is punctured with a trocar or needle and insufflated to secure the anatomic working space in the abdomen in the laparoscopic procedures. However, it requires an airtight surgical system during the operative procedure.

The conventional open surgical procedure has a drawback since it requires rather a large incision to visualize and secure the anatomic working space, which is critical for cosmetic and postoperative results. Similarly, the conventional laparoscopic procedure requires an airtight system, so that it necessitates an airtight trocar and a set of expensive equipment solely developed for such a trocar. More importantly, a gas insufflation procedure is extremely painful to the patient and requires general anesthesia of the patient.

SUMMARY OF THE INVENTION

Accordingly, the present invention is directed to surgical instruments and a method for creating an anatomic working space in a minilaparotomy procedure that substantially obviates one or more of problems due to limitations and disadvantages of the related art.

Another object of the present invention is to provide surgical instruments and a method for creating an anatomic working space in a minilaparotomy procedure to minimize a laparoscopic incision.

Another object of the present invention is to provide surgical instruments and a method for creating an anatomic working space in a minilaparotomy procedure without gas insufflation.

Another object of the present invention is to provide surgical instruments and a method for creating an anatomic working space in a minilaparotomy procedure in a retroperitoneal space.

Another object of the present invention is to provide surgical instruments and a method for creating an anatomic working space in a minilaparotomy procedure in a peritoneal space.

Another object of the present invention is to provide surgical instruments and a method for creating an anatomic working space in a minilaparotomy procedure to minimize an invasive procedure.

Another object of the present invention is to provide surgical instruments and a method for creating an anatomic working space in a minilaparotomy procedure that substantially reduces medical costs and patient's recovery time.

Another object of the present invention is to surgical instruments and a method for creating an anatomic working space in a minilaparotomy procedure that can be readily utilized by surgeons.

Another object of the present invention is to provide surgical instruments and a method for creating an anatomic working space in a minilaparotomy procedure that can be accomplished by both a direct vision and a telescopic monitoring.

A further object of the present invention is to provide surgical instruments and a method for creating an anatomic working space in a minilaparotomy procedure that can be used in a laparoscopic surgery.

Additional features and advantages of the invention will be set forth in the description which follows and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a method for creating an anatomic working space in a body for a minilaparotomy procedure includes forming a minilaparotomy opening in the body, forming a trocar opening in the body, inserting a trocar into the trocar opening, introducing a telescope through the trocar to observe a first tissue to be surgically treated, inserting at least one first piercing retractor into the body through the minilaparotomy opening, wherein the piercing retractor has first and second end portions, puncturing a wall of the body by the first end portion of the first piercing retractor, and lifting the wall of the body and moving around by using the first piercing retractor until a desirable anatomic working space is created in the body.

In another aspect of the present invention, a surgical instrument for creating an anatomic working space in a body for a minilaparotomy procedure includes a piercing retractor for lifting a wall of the body and having first and second end portions, wherein the first end portion has an end sharp enough to puncture the wall of the body without using an additional surgical instrument and the second end portion has a blade wide enough to lift the wall of the body without damaging the wall to create the anatomic working space.

In another aspect of the present invention, a surgical instrument for creating an anatomic working space in a body for a minilaparotomy procedure includes a piercing retractor for holding back tissues, relocating a first tissue to be surgically treated to provide the anatomic working space, wherein the piercing retractor has first and second end portions, and the first end portion has an end sharp enough to puncture the wall of the body without an additional surgical instrument and the second end portion has a blade wide enough to hold back at least one second tissue and relocate the surgically treated tissue to the anatomic working space.

In another aspect of the present invention, a surgical instrument for creating an anatomic working space in a body for a minilaparotomy procedure includes a forceps for holding a surgically treated tissue through a laparoscopic opening, wherein the forceps has an angled handle wide enough to directly reach the surgically treated tissue through the laparoscopic opening.

In a further aspect of the present invention, a surgical instrument for creating an anatomic working space in a body for a minilaparotomy procedure includes a needle driver for holding a needle through a minilaparotomy opening, wherein the needle driver has an angled handle wide enough to directly reach the surgically treated tissue through the laparoscopic opening.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention.

In the drawings.

DETAILED DESCRIPTION OF THE ILLUSTRATED EMBODIMENTS

Reference will now be made in detail to the illustrated embodiments of the present invention, examples of which are illustrated in the accompanying drawings. Wherever possible, the same reference numbers will be used throughout the drawings to refer to the same or like parts.

Figure 1:
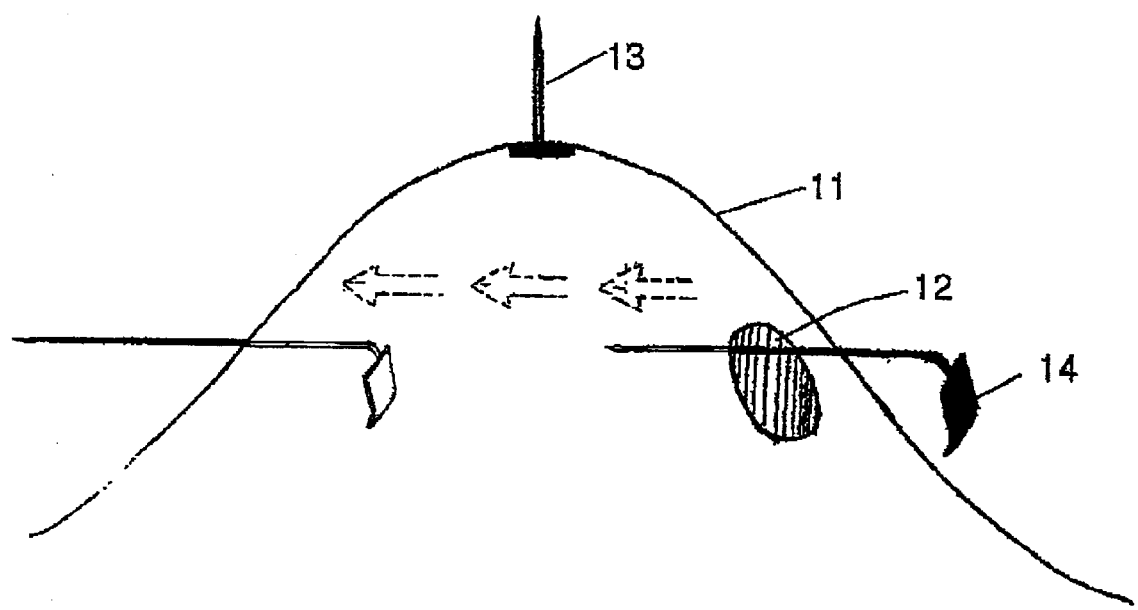
FIG. 1 is a schematic view of an anatomic working space created in an abdomen by using piercing retractors through a minilaparotomy opening in an abdominal wall according to the present invention.

FIG. 1 illustrates a schematic view of an anatomic working space created in a patient's abdomen by using piercing retractors through a minilaparotomy incision in an abdominal wall according to the present invention. Although the abdominal area is illustrated and described in the present invention as an example, the present invention may also be applicable to other parts of the body.

General anesthesia is given to the patient prior to an incision. As shown in FIG. 1, about 3 to 10 cm transverse skin incision 12 for the laparoscopic opening is made into a body wall 11. First and second piercing retractors 13 and 14 may be used in the present invention. One end of the first and second piercing retractors 13 and 14 has a sharp tip to puncture the body wall 11 without using any additional surgical instruments.

The first and second piercing retractors 13 and 14 are introduced into the patient's abdomen through the skin incision 12. The sharp end of the first and second piercing retractors 13 and 14 punctures the body wall 11 and is lifted up to the direction (shown as arrows in FIG. 1) to the body wall 11 until the other end touches the body wall 11. The other end of the piercing retractors 13 and 14 are shaped in a different fashion. The first piercing retractor 13 is mainly used to lift up the body wall 11 to create an anatomic working space in the body. On the other hand, the second piercing retractor 14 is primarily engaged to hold back the tissues around the area to be surgically treated. Detailed descriptions for these surgical instruments will be made with reference to FIGS. 5 to 7.

The piercing retractors 13 and 14 may be secured to an electrically controlled abdominal wall elevator (not shown) through a metal bar. Alternatively, a grip (shown in FIG. 7) may be connected to the sharp end of the piercing retractors 13 and 14, so that it facilitates manipulation of the piercing retractors in the minilaparotomy procedure.

Figure 2:
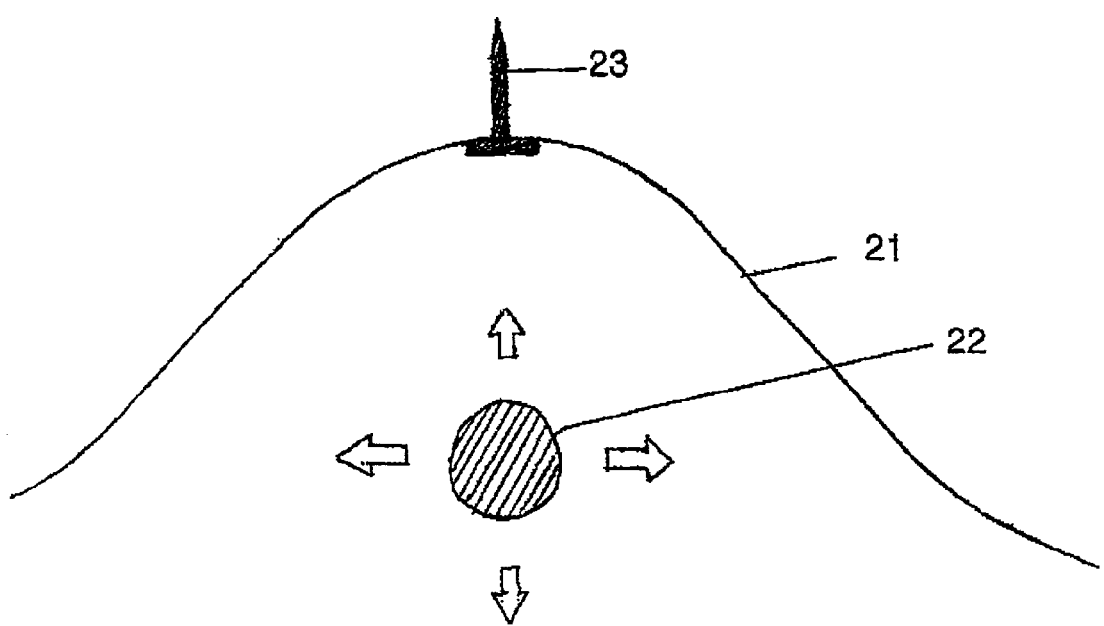
FIG. 2 is a schematic view of the abdomen illustrating that a position of the minilaparotomy opening is easily moved by moving around the piercing retractor according to present invention.

FIG. 2 illustrates that a position of a laparoscopic opening 22 in the body wall 11 may be readily relocated by lifting up a piercing retractor 23 to various directions according to the present invention. Thus, an exposure of the surgical area maybe maximized through the minilaparotomy opening 22, so that it provides the operator with a higher degree of freedom in the operative procedure.

Figure 3:
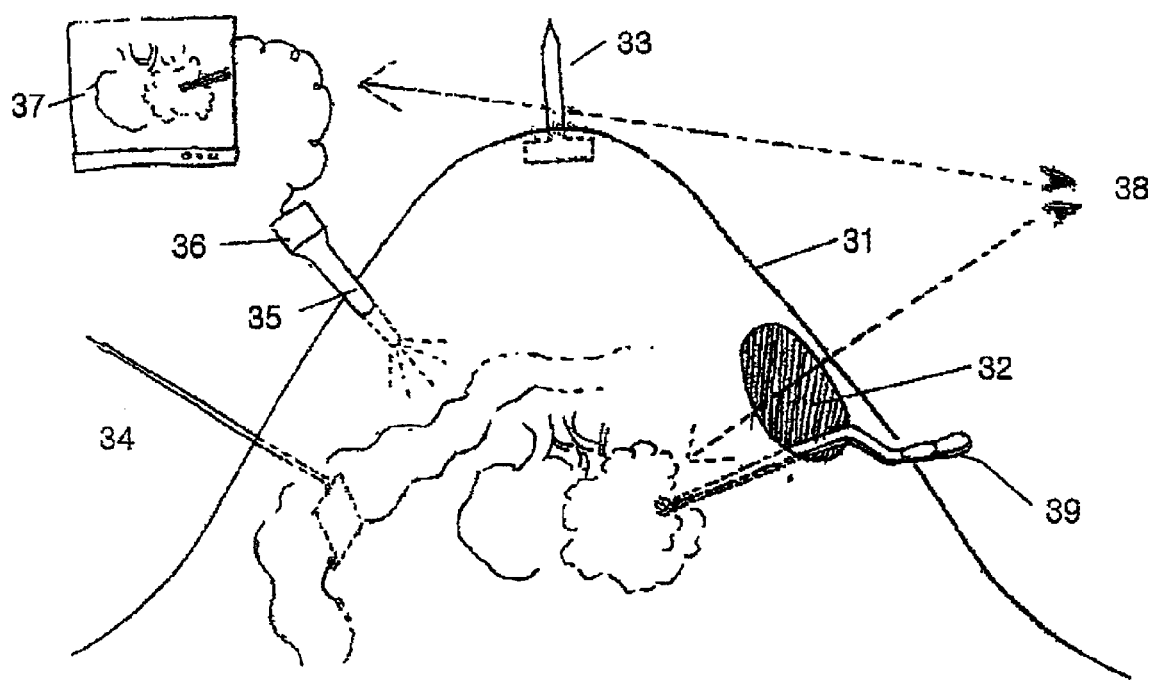
FIG. 3 is a schematic view of the abdomen illustrating the use of both telescope and naked eyes to visualize a surgically treating area according to the present invention.

In order to more effectively visualize the surgical area, a telescope 36 and naked eyes 38 may be used simultaneously. A 1.5 cm long skin stab is made at an appropriate position in the body wall 31, as shown in FIG. 3. For example, the stab is deepened by a tonsil clamp. A trocar 35 is introduced into a skin stab for a minilaparotomy opening 32. For example, a Hassan balloon trocar with 30 cc ballooning may be used in the present invention. The telescope 36 is introduced into the skin stab through the trocar 35. For facilitating the surgery, a forceps 39 is used for holding back the tissues to be treated or around the surgical area directly through the minilaparotomy opening 32. Also, first and second piercing retractors 33 and 34 are employed, similar to FIGS. 1 and 2, while the surgical area is observed either directly through the minilaparotomy opening 32 or by a video monitor 37.

Figure 4:
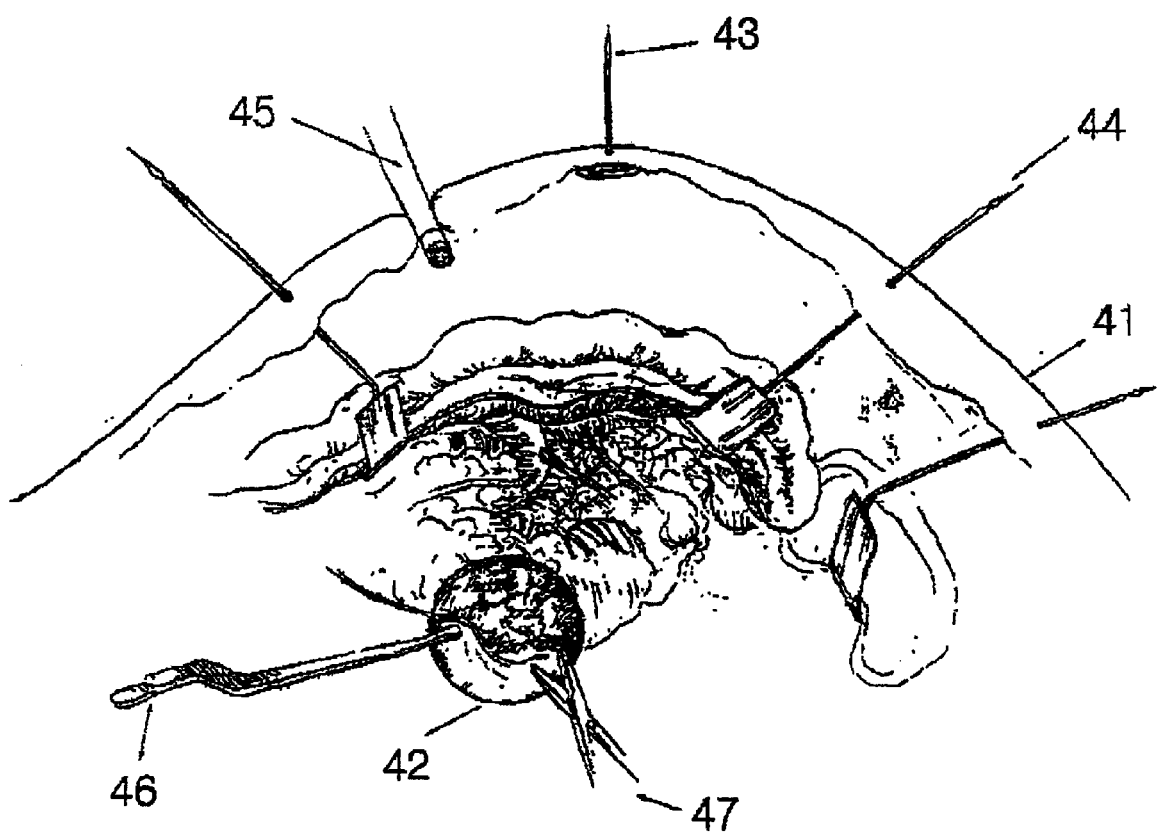
FIG. 4 is a transverse cross-sectional view of the abdomen illustrating the overall operative structures in use of the piercing retractors to create an anatomic working space according to the present invention.

FIG. 4 is a transverse cross-sectional view of the abdomen illustrating the overall operative structure in use of the piercing retractors to create an anatomic working space according to the present invention.

As shown in FIG. 4, a body wall 41 is punctured by a first piercing retractor 43 and at least one second piercing retractor 44. The body wall 41 is lifted up by the first piercing retractor 43. Another puncture may be made with the first piercing retractor 43 and a grip (shown in FIG. 7) of the first piercing retractor 43 is connected to the end of the first piercing retractor 43. By pulling the grip of the piercing retractor, more surgical space is generated in the body. The second piercing retractor 44 holds back the tissues to be treated at the surgical area or the tissues around the surgical area. Using a telescope 45 through a trocar, the surgical area is observed by the operator. At the same time, the operator may observe the area of interest by his naked eyes. In addition, a forceps 46 and a needle driver 47 may also be used to hold back the tissues to be treated at the surgical area or the tissues around the surgical area in order to facilitate the operative procedure.

Figure 5:
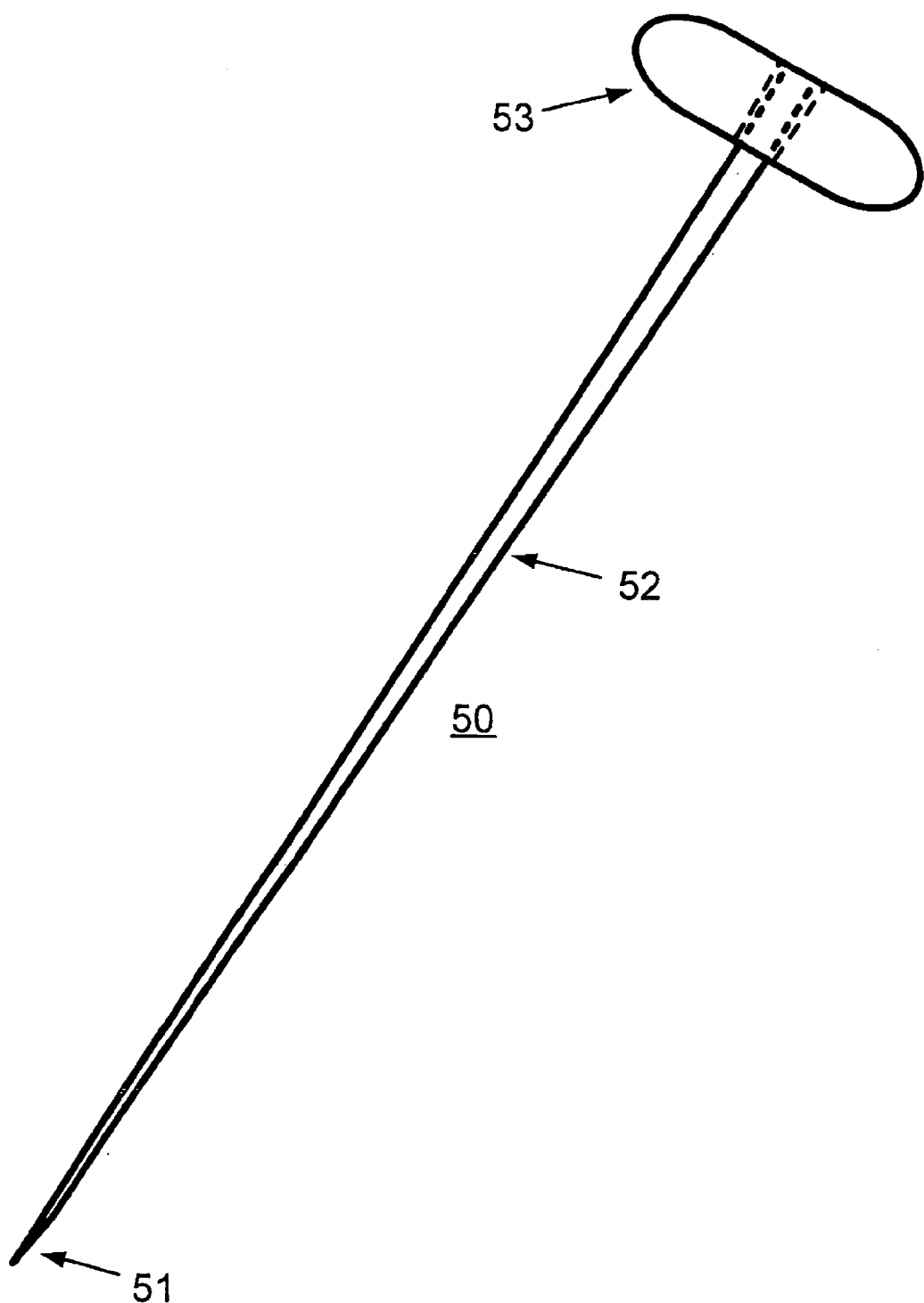
FIG. 5 is a schematic perspective view of a first piercing retractor for lifting up the abdominal wall according to the present invention.

FIG. 5 is a schematic perspective view of a first piercing retractor for holding back the tissues according to the present invention.

A first piercing retractor 50 of FIG. 5 is a surgical instrument to provide an anatomic working space within the body in the operative procedure. The first piercing retractor 50 has a sharp end portion 51, a blade portion 53, and a middle portion 52 between the sharp end portion 51 and the blade portion 53. The middle portion 52 and the blade portion 53 may be attached by welding or any other feasible processes in industry. Alternatively, the middle portion 52 may be attached to the blade portion 53 without any permanent joint. For example, the sharp end portion 51 and the middle portion 52 pass through a hole formed in the blade portion 53. The size of the hole is slightly less than the diameter of the middle portion 52 and greater than the sharp end portion 51. Thus, the middle portion 52 may stick to the blade portion 53, since the operator always pulls the first piercing retractor 50 to the opposite direction of the blade portion 53 in operation. Also, the connection may be joined by a snap in fitting.

Since the sharp end portion 51 is used to puncture the body wall, it should be acute enough to puncture the body wall without any pretreatment on the body wall. The middle portion 52 is a thin straight rod, so that it can easily penetrate the hole made by the sharp end portion. The blade portion 53 should be wide enough, so it can hold up the body wall without damaging the body wall and the hole. Also, the blade portion 53 is narrow enough to easily pass through the minlaparotomy opening. The blade portion may be formed to have any kind of shapes including oval and circle. For example, the minilaparotomy opening may be made to be about 7 to 10 cm in the present invention. The first piercing retractor 50 may be made of a surgical stainless steel and used as a disposable device.

Figure 6:
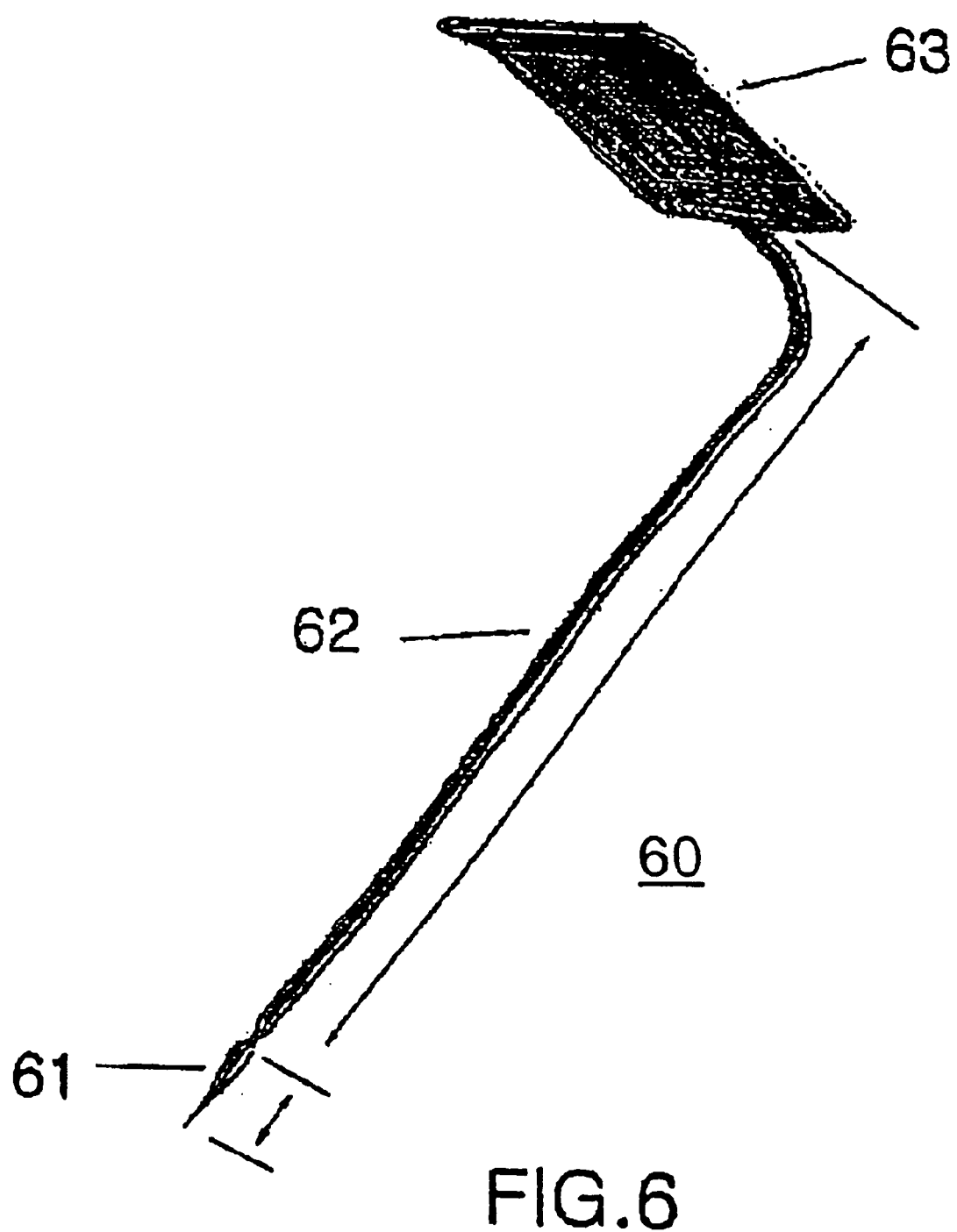
FIG. 6 is a schematic perspective view of a second piercing retractor for holding back the tissues according to the present invention.

FIG. 6 is a schematic perspective view of a second piercing retractor for lifting up the abdominal wall according to the present invention.

A second piercing retractor 60 of FIG. 6 is a surgical instrument to provide an anatomic working space within the body in the operative procedure. Similar to the first piercing retractor 50, the second piercing retractor 60 has a sharp end portion 61, a blade portion 63, and a middle portion 62 between the sharp end portion 61 and the blade portion 63. The middle portion 62 and the blade portion 63 may be attached by welding or any other feasible processes in the industry. Alternatively, the middle portion 52 may be attached to the blade portion 53 without any permanent joint. For example, the sharp end portion 51 and the middle portion 52 pass through a hole formed in the blade portion 53. The size of the hole is slightly less than the diameter of the middle portion 52 and greater than the sharp end portion 51. Thus, the middle portion 52 may stick to the blade portion 53, since the operator always pulls the first piercing retractor 50 to the opposite direction of the blade portion 53 in operation.

Since the sharp end portion 61 is used to puncture the body wall, it should be acute enough to puncture the body wall without any pretreatment on the body wall as described in the first piercing retractor 50. The middle portion 62 is a thin straight rod, so that it can easily penetrate the hole made by the sharp end portion 61. Also, the other end of the middle portion 62 is bent with an angle. The blade portion 63 should be wide enough, so it can hold back the tissues to be surgically treated or the tissues around the surgical area. Also, the blade portion 63 is narrow enough to easily pass through the minilaparotomy opening. The blade portion 63 may be formed to have any kind of shapes including square and rectangle. For example, the minilaparotomy opening may be made to be less than about 7 cm in the present invention. The first piercing retractor 60 may be made of a surgical stainless steel and used as a disposable device.

Figure 7:
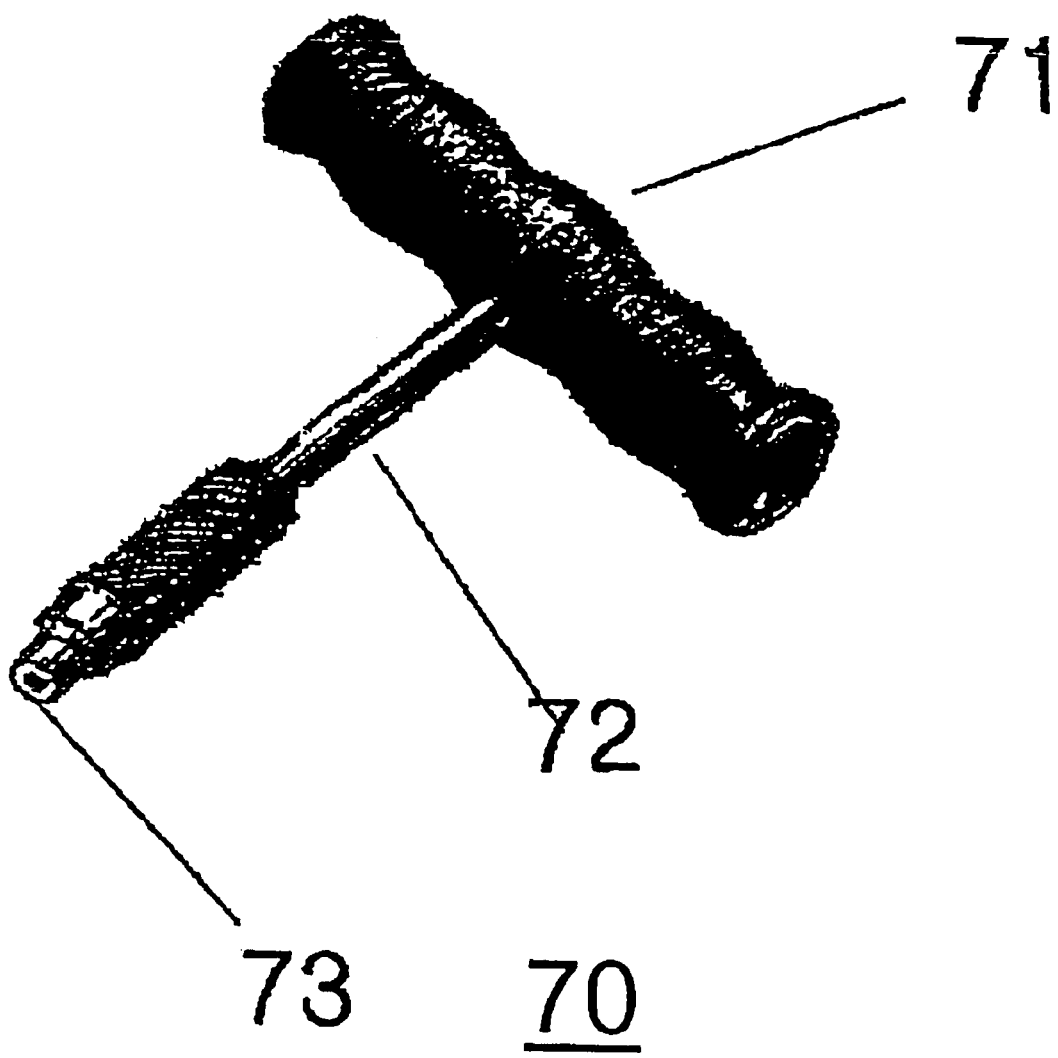
FIG. 7 is a schematic perspective view of a grip for securing one end of the piercing retractors of FIGS. 5 and 6.

FIG. 7 is a schematic perspective view of a grip for securing the sharp end of the first and second piercing retractors of FIGS. 5 and 6.

A grip 70 of FIG. 7 is a surgical instrument that can be used with the first and second piercing retractors 50 and 60. The grip 70 includes a handle portion 71, a middle portion 72, and a connecting portion 73. Since the first and second piercing retractors 50 and 60 have the sharp end portions, the connecting portion 73 may be coupled to the sharp end portions of the first second piercing retractors 50 and 60 for the operator's convenience and efficiency in the operative procedure.

The handle portion 71 is shaped to provide the operator or the assistant with a convenient grip. The connecting portion 73 may be formed of any kind of fasteners for binding the first piercing retractor 50 and the grip 70. The middle portion 72 is a straight rod connecting the handle portion 71 and the connecting portion 73. The grip 70 except for the handle portion 71 may be made of a surgical stainless steel and used as a disposable device.

Figure 8:
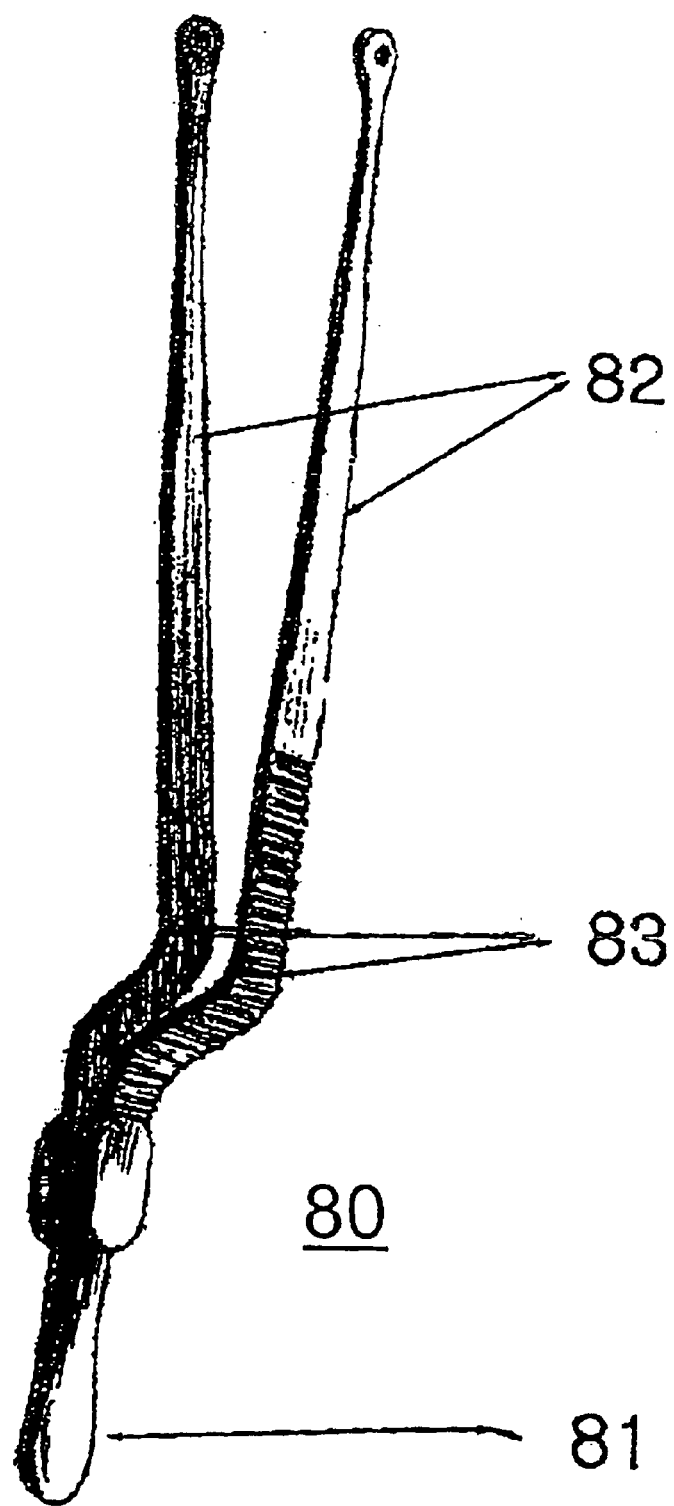
FIG. 8 is a schematic perspective view of a forceps with an angled handle for manipulating the tissues through the laparoscopic opening according to the present invention.

FIG. 8 is a schematic perspective view of a forceps with an angled handle. The forceps 80 is to manipulate the tissues directly through the minilaparotomy opening. The forceps 80 comprises a stem 81 bifurcated to a pair of open portions 82 and a bent handle portion 83 to be grabbed by the operator or the assistant. In order to reach the tissues through the small minilaparotomy opening, the forceps 80 should have enough length and angle to directly reach the tissues without any visual disturbance of the operative field. For example, the bent handle portion 83 has an angle of about 15° to 60° from the open portions 82. Also, the bent handle portion 83 has a rough surface to provide a better handgrip to the operator or the assistant. The forceps 80 may be made of a surgical stainless steel and used as a disposable device.

Figure 9:
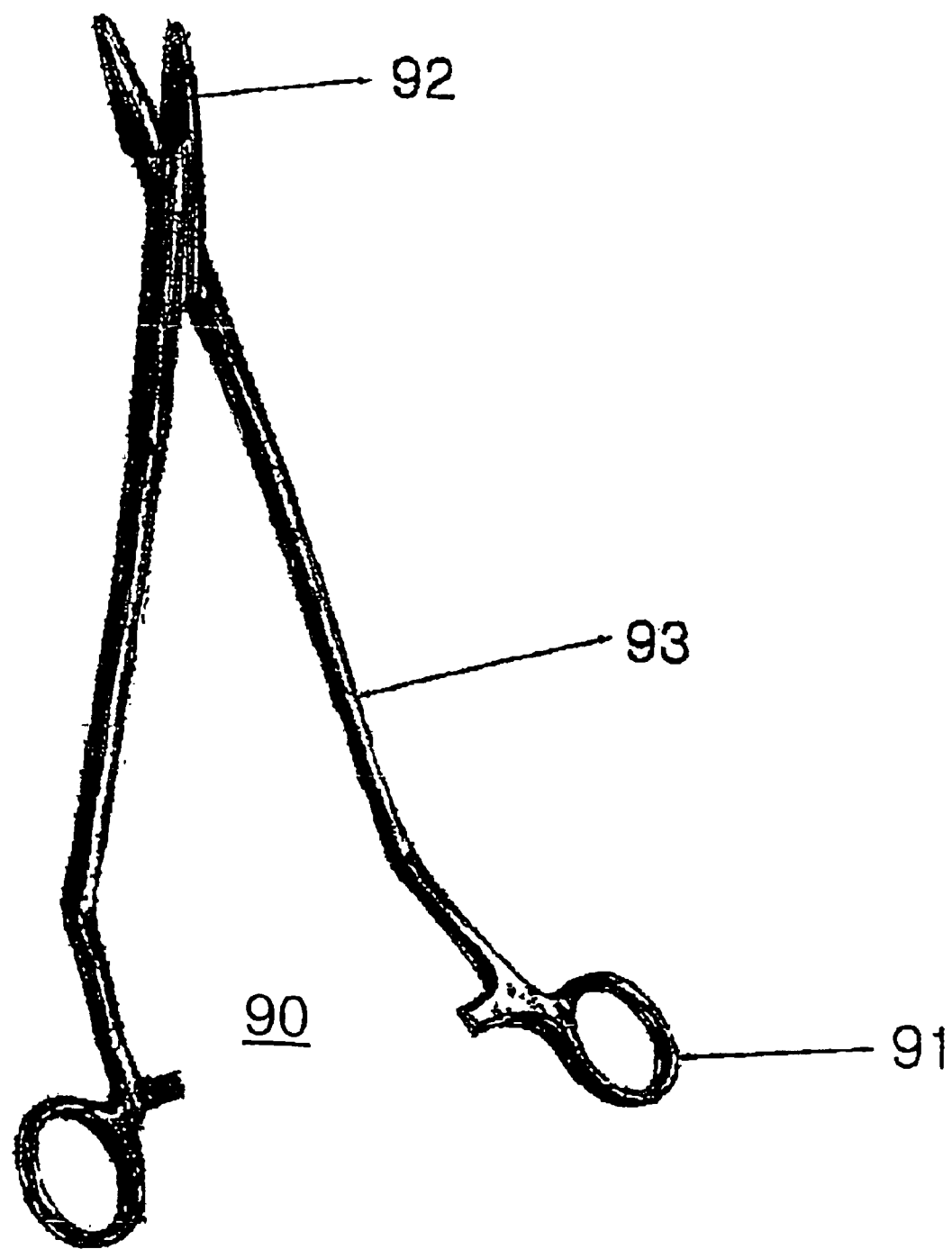
FIG. 9 is a schematic perspective view of a needle driver with an angled handle for manipulating the tissues through the laparoscopic opening according to the present invention.

A needle driver with an angled handle is illustrated in FIG. 9. Similar to the forceps 80 of FIG. 8, the needle driver 90 is to manipulate the tissues directly through the minilaparotomy opening. The needle driver 90 comprises a pair of finger holders 91, a pair of grips 92, and middle portions 93 connecting the finger holders 91 and the grips 92. The finger holders 91 are bent to have an angle. The finger holders 90 should have enough length and angle to directly reach the tissues without any visual disturbance of the operative field. For example, the angle is in the range of about 15° to 60° with respect to the middle portions 93 and the grips 92. The finger holders 91 is held by operator's or assistant's fingers in the operative procedure. The needle driver 90 may be made of a surgical stainless steel and used as a disposable device.

The above-mentioned surgical method and instruments in the minilaparotomy procedure may be applied to any one of a general surgical procedure, extraperitoneal and transperitoneal kidney surgical procedures, adrenal surgical procedures, a bladder surgical procedure, transperitoneal and extraperitoneal prostate surgical procedures, transperitoneal and extraperitoneal ureter surgical procedures, a gynecologic procedure, a vascular surgical procedure, aortic and caval surgical procedures, an adrenal surgical procedure, a transplant surgical procedure, a neurosurgical surgical procedure, and an orthopedic surgical procedure.

More specifically, in the above-described surgical procedures, the general procedure may be applied to any one of liver, pancreas, gall bladder, spleen, stomach, small bowel, large bowel, and rectum. The extraperitoneal kidney surgical procedure may be applied to any one of nephrectomy, live donor nephrectomy, radical nephrectomy, nephrolithotomy, cyst marsupialization and partial nephrectomy. The transperitoneal kidney surgical procedure may be applied to any one of nephrectomy, live donor nephrectomy, radical nephrectomy, nephrolithotomy, and partial nephrectomy. The bladder surgical procedure may be applied to any one of transperitoneal, extraperitoneal, cystectomy, cystotomy, urinary diversion such as ureterocutaneostomy and ileal/colon conduit and vesicolithotomy. The prostate surgical procedure may be applied to any one of radical prostatectomy and suprapubic prostatectomy. The transperitoneal and extraperitoneal ureter surgical procedures may be applied to any one of ureterolithotomy, ureteroureteostomy, ureterocalicostomy, calycorraphy, calycoplasty and ureteopyeloplasty. The gynecologic procedure may be applied to one of uterus, ovaries, fallopian tubes, and vagina. The vascular surgical procedure may be applied to any one of arteries and veins and retroperitoneal lymph node dissection. The transplant surgical procedure may be applied to any one of liver, pancreas, small and large bowels, and kidney. The neurosurgical surgical procedure may be applied to any one of spine, spinal cord, and peripheral nerves. The orthopedic surgical procedure may be applied to one of spine, spinal cord, and osseous structures.

It will be apparent to those skilled in the art that various modifications and variations can be made in the surgical instruments and the method for creating an anatomic working space for minilaparotomy procedure with a piercing retractor in the present invention without departing from the spirit or scope of the inventions. Thus, it is intended that the present invention covers the modifications and variations of this invention provided they come within the scope of the appended claims and their equivalents.

What is claimed is:

1. A method for creating an anatomic working space in a body for a minilaparotomy procedure, comprising:
   inserting at least one first piercing retractor into the body through a minilaparotomy opening, wherein the first piercing retractor has first and second end portions;
   puncturing a wall of the body with the first end portion of the first piercing retractor such that the first end portion protrudes from the body and the second end portion is within the body; and
   lifting the wall of the body using the first piercing retractor and moving around the second end portion of the first piercing retractor within the body until enough anatomic working space is created in the body to treat a first tissue.

2. The method according to claim 1, further comprising:
   inserting at least one second piercing retractor through the opening, wherein the second piercing retractor has first and second end portions;
   puncturing the wall of the body by the first end portion of the second piercing retractor such that the first end portion protrudes from the body; and
   holding back at least one second tissue by using the second end portion of the second piercing retractor to expose a first tissue.

3. The method according to claim 1, further comprising holding the first tissue by a forceps with a bent handle through the minilaparotomy opening.

4. The method according to claim 1, further comprising holding the first tissue by a needle driver with a bent handle through the minilaparotomy opening.

5. The method according to claim 1, further comprising connecting a grip to the first piercing retractor prior to lifting the wall of the body to create a desirable anatomic working space.

6. The method according to claim 1, further comprising securing the first end portion of the first piercing retractor to a retractor bar.

7. The method according to claim 1, wherein the minilaparotomy opening is cut to be about 7 to 10 cm.

8. The method according to claim 1, wherein the first end portion of the first and second piercing retractors have an end sharp enough to puncture the wall of the body without using an additional surgical instrument.

9. The method according to claim 1, wherein the second end portion of the first piercing retractor has a blade wide enough to lift the wall of the body without damaging the wall.

10. The method according to claim 1, wherein the second end portion of the first piercing retractor is detachable.

11. The method according to claim 1, wherein the second end portion of the second piercing retractor has a blade wide enough to hold back the second tissue.

12. The method according to claim 1, wherein the minilaparotomy procedure is applied to one of a general surgical procedure, extraperitoneal and transperitoneal kidney surgical procedures, adrenal surgical procedures, a bladder surgical procedure, transperitoneal and extraperitoneal prostate surgical procedures, transperitoneal and extraperitoneal ureter surgical procedures, a gynecologic procedure, a vascular surgical procedure, aortic and caval surgical procedures, an adrenal surgical procedure, a transplant surgical procedure, a neurosurgical surgical procedure, and an orthopedic surgical procedure.

13. The method according to claim 12, wherein the general procedure is applied to one of liver, pancreas, gall bladder, spleen, stomach, small bowel, large bowel, and rectum.

14. The method according to claim 12, wherein the extraperitoneal kidney surgical procedure is applied to one of nephrectomy, live donor nephrectomy, radical nephrectomy, nephrolithotomy, cyst marsupialization and partial nephrectomy.

15. The method according to claim 12, wherein the transperitoneal kidney surgical procedure is applied to one of nephrectomy, live donor nephrectomy, radical nephrectomy, nephrolithotomy, calicoplasty, calicorraphy and partial nephrectomy.

16. The method according to claim 12, wherein the bladder surgical procedure is applied to one of transperitoneal, extraperitoneal, cystectomy, cystotomy, urinary diversion using ileum or colon and vesicolithotomy.

17. The method according to claim 12, wherein the prostate surgical procedure is applied to one of radical prostatectomy and suprapubic prostatectomy.

18. The method according to claim 12, wherein the transperitoneal and extraperitoneal ureter surgical procedures are applied to one of ureterolithotomy, ureteroureteostomy, calicoureterostomy and ureteopyeloplasty.

19. The method according to claim 12, wherein the gynecologic procedure is applied to one of uterus, ovaries, fallopian tubes, and vagina.

20. The method according to claim 12, wherein the vascular surgical procedure is applied to one of arteries and veins.

21. The method according to claim 12, wherein the transplant surgical procedure is applied to one of liver, pancreas, small and large bowels, and kidney.

22. The method according to claim 12, wherein the neurosurgical surgical procedure is applied to one of spine, spinal cord, and peripheral nerves.

23. The method according to claim 12, wherein the orthopedic surgical procedure is applied to one of spine, spinal cord, and osseous structures.

24. The method according to claim 1, further comprising:
   a procedure prior to inserting the at least one first piercing retractor including:
      forming a minilaparotomy opening in the body;
      forming a trocar opening in the body;
      inserting a trocar into the trocar opening; and
      introducing a telescope through the trocar to observe and illuminating a first tissue to be surgically treated.

25. A surgical instrument for creating an anatomic working space in a body for a minilaparotomy procedure, comprising:
   a piercing retractor for lifting a wall of the body and having first and second end portions, wherein the first end portion has an end sharp enough to puncture the wall of the body without using an additional surgical instrument and a blade at the second end portion that has a blade wide enough to lift the wall of the body without damaging the wall to create the anatomic working space; and
   one of a grip and a retractor bar secured to the first end portion of the piercing retractor, wherein the blade has a through-hole having a diameter greater than the first end portion and smaller than the second end portion.

* * * * *